United States Patent [19]

Stagi et al.

[11] 4,006,178
[45] Feb. 1, 1977

[54] PROCESS FOR THE MANUFACTURE OF DICYANOVINYL COMPOUNDS

[75] Inventors: Mauro Stagi, Saronno, (Varese), Italy; Tibor Somlo; Frantisek Gaspar, both of Birsfelden, Switzerland

[73] Assignee: Ciba-Geigy Corporation, Ardsley, N.Y.

[22] Filed: Mar. 27, 1975

[21] Appl. No.: 563,006

Related U.S. Application Data

[63] Continuation-in-part of Ser. No. 290,024, Sept. 18, 1972, abandoned.

[30] Foreign Application Priority Data

Sept. 24, 1971 Switzerland ............... 13992/71
Aug. 15, 1972 Switzerland ............... 12093/72

[52] U.S. Cl. .............. 260/465 D; 260/251 R; 260/283 CN; 260/287 T; 260/307 R; 260/309.6; 260/310 R; 260/310 A; 260/319.1; 260/326.8; 260/329 R; 260/329 AM; 260/346.1 R; 260/465 E; 260/465.4

[51] Int. Cl.² .............. C07D 215/06; C07C 121/54

[58] Field of Search ... 260/283 CN, 465 H, 329 AM, 260/310 R, 346.1 R, 465 D, 465 E

[56] References Cited

UNITED STATES PATENTS

B403,076  4/1976  Carter.................... 260/465 E

OTHER PUBLICATIONS

Stagi et al., Chem. Abstr., vol. 78:159283h; (1973).

Primary Examiner—Donald G. Daus
Assistant Examiner—Mary C. Vaughn
Attorney, Agent, or Firm—Joseph G. Kolodny; Edward McC. Roberts; Prabodh I. Almaula

[57] ABSTRACT

Process for the manufacture of aromatic, heteroaromatic or aliphatic compounds which contain at least one radical of the formula

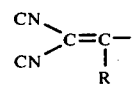

wherein R denotes a hydrogen atom or an alkyl, cycloalkyl or aralkyl radical, characterized in that an aromatic or heteroaromatic compound, which carries one or more electron-donating substituent with negative Brown substitution constants $\delta_p^+$ and without mobile hydrogen atoms, a π-excess-hetero-aromatic compound or a CH-acid compound is reacted with a 2,2-dicyanoethylene of the formula

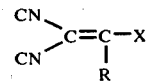

wherein X is a halogen atom, preferably chlorine or bromine, and R has the abovementioned meaning, without the presence of Lewis acids, in an anhydrous, preferably organic, medium, with an acid-binding agent optionally being added as a further component.

8 Claims, No Drawings

PROCESS FOR THE MANUFACTURE OF DICYANOVINYL COMPOUNDS

This application is a continuation-in-part of application Ser. No. 290,024, filed Sept. 18, 1972, now abandoned.

The present invention relates to a new process for the manufacture of aromatic, hetero-aromatic or aliphatic dicyanovinyl compounds which contain at least one group of the formula

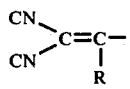

wherein R preferably denotes hydrogen or an aralkyl, cycloalkyl or preferably low-molecular alkyl group.

It is known to manufacture such compounds, especially those wherein R denotes hydrogen, by condensing an appropriate aldehyde with malodinitrile. The requisite aldehydes must be manufactured first, for example by a Vilsmeier reaction, so that 2 reaction steps are necessary in order to arrive at the desired dicyanovinyl compounds. It is furthermore known from the literature [K. Friedrich, Synthesis 1970, page 23] that 1-chloro-2,2-dicyanoethylene permits the introduction of the dicyanovinyl group into an aromatic nucleus by means of a Friedel-Crafts reaction. This reaction can however only be employed when the compound into which the dicyanovinyl group is to be introduced does not contain any substituents or groups which can react with the Lewis acids, for example anhydrous aluminum chloride or zinc chloride, used as catalysts in the Friedel-Crafts reaction described. For this reason it is not readily possible to react aromatic compounds which are substituted, for example, by tertiary amino groups, with 1-chloro-2,2-dicyanoethylene in accordance with the process described by K. Friedrich, since the amino group forms complexes with the catalysts used.

It has now been found, surprisingly, that in cases where an aromatic or hetero-aromatic nucleus is sufficiently activated, by electron-donating substituents (1st order substituents), for an electrophilic attack, the introduction of the dicyanovinyl group is also possible without addition of Lewis acids, that is to say without a catalyst. As a measure of the tendency of the substituents to supply electrons into the $\pi$-system of the aromatic ring it is possible to use the Hammet substitution constants $\delta_p$ or $-$ since in the new electrophilic substitution reaction conjugative effects must also be taken into account — preferably the constants $\delta_p{}^+$ modified according to Brown. The smaller these constants are, the greater is the electron-donating action of the substituents. More detailed information on these values and their calculation is to be found in J. Hine, Physical Organic Chemistry, 1st Edition, pp. 69–80, 1956, McGraw-Hill Book Co. (see also German translation, 2nd Edition, 1966, page 88, Georg Tieme Verlag, Stuttgart); R. W. Alder, R. Baker and J. M. Brown, Mechanism in Organic Chemistry, pp. 30–34, Wiley-Interscience, London, New York 1971; P. R. Wells, Linear free energy relationships, Academic Press, London and New York 1968. Possible substituents of aromatic and heteroaromatic compounds into which a dicyanovinyl group is to be introduced in accordance with the process of the invention are those with negative $\delta_p{}^+$ values, the reaction proceeding the more easily, the smaller, that is to say the more negative, the $\delta_p{}^-$ values are. Dialkylamino, alkoxy and thioalkyl groups are particularly favourable.

In the case of the $\pi$-excess-hetero-aromatic compounds, that is to say hetero-aromatic compounds with a negative net charge on the carbon atoms and a correspondingly positive charge on the hetero-atom, such as nitrogen, oxygen or sulphur, no electron-donating substituents are necessary for introducing a dicyanovinyl group without catalyst since such heterocyclic compounds are already sufficiently active. Typical representatives of the $\pi$-excess-heterocyclic compounds are the pyrroles, pyrazoles, imidazoles, indoles, furanes, thiophenes and oxazoles. Further data, in particular also charge distribution diagrams, are to be found in A. Albert, Heterocyclic Chemistry, The Athlone Press, London 1959 (German translation: Chemie der Heterocyclen, Verlag Chemie GmbH, Weinheim 1962) or M. H. Palmer, The Structure and Reactivity of Heterocyclic Compounds, Edward Arnold, London 1967.

It has furthermore been found that the introduction of a dicyanovinyl group with dicyanoethylenes is also possible in CH-acid compounds, i.e. in compounds containing an active methylene group, in which case their alkali salts are reacted, if appropriate.

To introduce a dicyanovinyl group, it is possible to use 2,2-dicyanoethylenes, which contain halogen in the 1-position, especially 1-bromo- and 1-chloro-2,2-dicyanoethylenes. A relatively cheap possible synthesis of the chlorine compound is already known (U.S. Pat. No. 2,774,783) so that this educt is preferred.

The process according to the invention is thus characterised in that an aromatic or hetero-aromatic compound, which carries one or more electron-donating substituent with negative Brown substitution constants $\delta_p{}^+$ and without mobile hydrogen atoms, a $\pi$-excess-hetero-aromatic compound or a CH-acid compound, is reacted with a 1-halogeno-2,2-dicyanoethylene of the formula

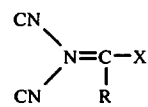

wherein X denotes a halogen atom, such as chlorine or bromine, and R denotes a hydrogen atom or an alkyl, cycloalkyl or aralkyl radical, without the presence of Lewis acids, in an anhydrous, preferably organic, medium, an acid-binding agent optionally being added as a further component. By alkyl there is above all meant $C_1$—$C_4$-alkyl, by cycloalkyl cyclohexyl is above all meant and by aralkyl benzyl is above all meant. The aromatic compounds are especially compounds of the benzene series, and the hetero-aromatic compounds are especially 6-membered nitrogen-containing heterocyclic compounds, such as pyridine, pyrimidine and pyridazine. As CH-acid compounds there should especially be mentioned benzyl cyanide, malonitrile, malonic acid esters, acetoacetic acid esters, phenylacetic esters, cyanoacetic acid esters, especially their low molecular alkyl esters, and optionally N-substituted or N,N-disubstituted acetoacetic acid amides.

The reaction is preferably carried out in anhydrous solvents of low dielectric constant, for the value of which 15 may be quoted as an upper limit. Aliphatic and aromatic, optionally chlorinated hydrocarbons are particularly suitable, for example methylene chloride, ethylene chloride, carbon tetrachloride, chloroform, benzene, toluene or chlorobenzene, as well as aliphatic ethers and low molecular fatty acids, for example glacial acetic acid.

The reaction temperature required for the introduction of the dicyanovinyl group depends greatly on the reactants and on the solvent used. Temperatures of about 0° C, preferably of 40° to 60° C, already suffice for the reaction of a N,N'-disubstituted m-toluidine with 1-chloro-2,2-dicyanoethylene in chlorobenzene. On the other hand, the same reaction with 1,3-dimethoxybenzene must be carried out at 120° to 140° C.

The aromatic or hetero-aromatic compounds can be used in a stoichiometric amount or in a two-fold to three-fold excess.

In the dicyanovinylation with 1-halogeno-2,2-dicyanoethylenes, hydrogen halide acid is liberated. If the starting compound contains basic groups, for example dialkylamino groups, the latter are protonised by the acid and the salt formed can no longer react with 1-halogeno-2,2-dicyanoethylenes. It is therefore necessary either to use the basic educt in an excess of 100% or again to liberate the base from the salt formed by adding an acid-binding agent for example triethylamine. However, compounds such as triethylamine must not come into contact with the 1-halogeno-2,2-dicyanoethylenes since they would react therewith in an undesired manner. In the process according to the invention, this problem has been solved by stepwise reaction of the starting material with 1-halogeno-2,2-dicyanoethylenes. Here half the basic starting material present is always reacted in each step, so that 50% is reacted in the first step, with the acid being trapped by the excess educt, with salt formation. Thereafter, an amount of triethylamine equivalent to the acid produced is added and the free base of the educt is recovered. In the steps which follow, half the basic starting material still present is again reacted in the same manner, that is to say 25% in the second step, 12.5% in the third step and so on, until 98.4% of the educt have been reacted after 6 steps. The addition of the 1-halogeno-2,2-dicyanoethylene and of the triethylamine can be controlled by means of a glass electrode.

If a compound into which a dicyanovinyl group is to be introduced contains no basic groups or at most weakly basic groups, the acid produced can be removed by means of a stream of gas. For this purpose, for example, nitrogen is passed through the solution.

A dicyanovinyl group can be introduced in accordance with the process of the invention especially into benzene derivatives and 6-membered nitrogen-containing heterocyclic compounds which contain, as electron-donating substituents, ether, thioether or tertiary amino groups which optionally form part of a heterocyclic ring. These groups preferably correspond to the formulae

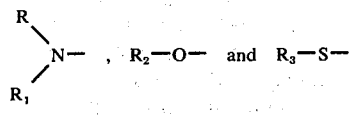

wherein R, $R_1$, $R_2$ and $R_3$ each denote an optionally substituted low molecular alkyl, cycloalkyl or aryl radical. Above all, the alkyl groups can carry substituents, for example aryl, cycloalkyl, low molecular alkoxy, low molecular alkylcarbonyloxy or alkylaminocarbonyloxy, as well as arylcarbonyloxy or arylaminocarbonyloxy, nitrile or halogen, especially chlorine.

Here, the term "low molecular" denotes a carbon content of 1 to 4 C atoms, phenyl and tolyl are especially meant by "aryl" and cyclohexyl is preferably meant by "cycloalkyl". The benzene derivative or heterocyclic compounds which have been mentioned can be joined to further fused carbocyclic or heterocyclic rings.

The aromatic nucleus of the benzene derivatives can contain yet further substituents in addition to the ether, thioether or amino groups listed, such as, for example, low molecular alkyl, alkoxy, alkanoylamino, alkoxycarbonylamino, carbalkoxy or benzoylamino radicals, halogen or halogenoalkyl, especially chlorine or trifluoromethyl.

The dicyanovinylation is of particular interest in the case of N,N-disubstituted anilines of which the nitrogen atom carries the substituents R and $R_1$ defined above and of which the aromatic nucleus can be substituted in the indicated manner. Such anilines correspond, for example, to the formula

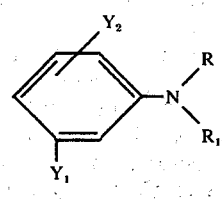

wherein $Y_1$ is hydrogen or a low molecular alkyl or alkoxy group, $Y_2$ is hydrogen, a low molecular alkyl, alkoxy, alkanoylamino, alkoxycarbonylamino or benzoylamino radical, chlorine or trifluoromethyl and R and $R_1$ have the indicated meaning.

In the case of the hetero-aromatic compounds of the furane, thiophene, isoxazole and pyrazole series, the above-mentioned electron-donating substituents are possible but not necessary, since these representatives of the π-excess-hetero-aromatic compounds easily undergo electrophilic substitution reactions. The introduction of a dicyanovinyl group in accordance with the process of the invention is thus possible, for example, in the following compounds: methoxybenzene, 1,3-dimethoxybenzene, 1-methyl-3-methoxy-benzene, dimethylaniline, 4-N,N-dimethylamino-6N-isopropylamino pyrimidine, 2-N,N-dimethylaminopyridine, methylthiobenzene, thiophene, furane, 2-methylfurane, 1-phenyl-3-methyl-pyrazolone, 1-(2'-chlorophenyl)-3-methyl-pyrazolone, 3-phenyl-isoxazolone, acetoacetic acid anilide, acetoacetic acid ethyl ester, cyanoacetic acid ethyl ester, N,N-dimethylacetoacetamide, acetoacetic acid-N-methylanilide, N-methyl-N-benzylaniline, N-methyl-N-β-cyanoethylaniline, N-ethyl-N-β-chloroethyl-aniline, N-ethyl-N-β-methoxyethylaniline, N,N-diethyl-3-trifluoromethylaniline, N,N-diethyl-3-acetylaminoaniline, N-ethyl-N-β-cyanoethyl-3-benzoylaminoaniline,

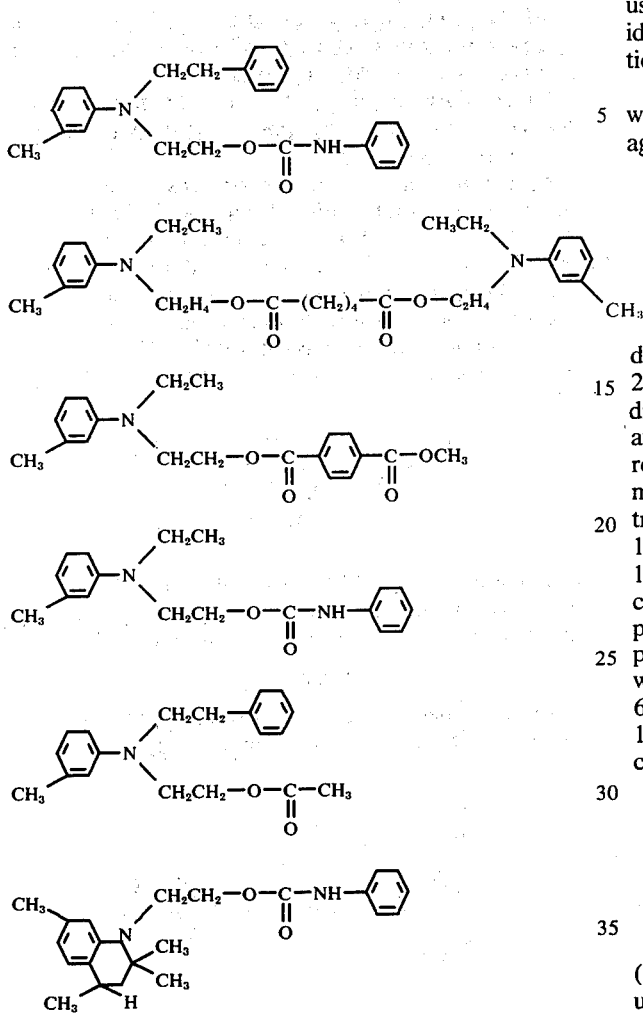

The unsubstituted 1-halogeno-2,2-dicyanoethylenes, above all 1-chloro-2,2-dicyanoethylene, are preferred because of their relatively easy accessibility.

The following known possibilities exist for the synthesis of the 1-halogeno-2,2-dicyanoethylenes: it is possible to condense malonic acid dinitrile with an ester and subsequently to introduce a chlorine or bromine atom by means of phosphorus oxychloride or phosphorus oxybromide. 1-Chloro-2,2-dicyanoethylene can furthermore appropriately be manufactured by pyrolysing 1-acetoxy-1,1-dicyanoethane according to U.S. Pat. No. 2,774,783 and passing chlorine into the reaction mixture, without isolating the 1,1-dicyanoethylene produced, and again pyrolysing the product.

The process according to the invention has the advantage that the introduction of a dicyanovinyl group into an aromatic or hetero-aromatic nucleus or into a CH-acid compound becomes possible in one step whilst hitherto an aldehyde group was first introduced, for example in a Vilsmeier reaction, and this group was condensed with malodinitrile in the subsequent step.

The reaction conditions are very mild; in many cases, the dicyanovinylation already proceeds smoothly at 20° to 40° C. A catalyst is not necessary. The yields are excellent.

The process according to the invention opens up a new method for the simple and cheap manufacture of important dyestuffs and intermediate products. The products obtained according to the invention can be used as intermediate products, as dyestuffs for polyamide and polyester fibres and as pigments, light protection agents or photosensitisers.

In the examples which follow the parts, unless otherwise stated, denote parts by weight, and the percentages denote percentages by weight.

EXAMPLE 1

41.5 parts of 1,3-dimethoxybenzene are first introduced into the reaction flask and heated to 120° C. 22.4 parts of a 50% strength solution of 1-chloro-2,2-dicyanoethylene in chlorobenzene are added dropwise at this temperature over the course of 1 hour. The resulting hydrochloric acid is constantly led away by means of a stream of nitrogen ($N_2$ stream) and is titrated as desired. After completion of the addition of 1-chloro-2,2-dicyanoethylene the mixture is heated to 140° C for a further hour. Thereafter the mixture is cooled to 10° C whilst stirring slowly, whereupon the product formed crystallises out. The yellow crystal paste is thereafter filtered off and the filter residue is washed with a little cold methanol and dried in vacuo at 60° to 70° C. In this way, 20.1 parts (94.1% relative to 1-chloro-2,2dicyanoethylene employed) of the analytically pure compound of the formula

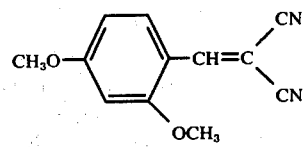

(melting point 141°–143° C) are obtained. If the product is recrystallised from methanol, yellow crystals of melting point 143° C are obtained.

If instead of 1-chloro-2,2-dicyanoethylene an equivalent amount of 1-bromo-2,2-dicyanoethylene is used and in other respects the procedure indicated above is followed, the compound having the indicated formula is again obtained.

EXAMPLE 2

24.2 parts of dimethylaniline are dissolved in 100 parts of anhydrous ether. A solution of 11.2 parts of 1-chloro-2,2-dicyanoethylene in 50 parts of anhydrous ether is added dropwise at 20° C over the course of 30 minutes, whilst stirring. The reaction mixture is boiled for 1 hour under reflux and is left to stand overnight at room temperature. The red-brown crystals are filtered off and washed with water until neutral. After drying, 14.7 parts (75%, relative to the 1-chloro-2,2-dicyanoethylene employed) of the compound of the formula

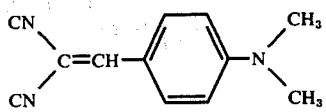

(melting point 179° C) are obtained.

If the 11.2 parts of 1-chloro-2,2-dicyanoethylene are replaced by 14.1 parts of 1-chloro-1-ethyl-2,2-dicyanoethylene (a) or 20.3 parts of 1-chloro-1-benzyl-2,2-dicyanoethylene (b) or 20.8 parts of 1-chloro-1-cyclohexyl-2,2-dicyanoethylene (c) or 19.4 parts of 1-chloro-1-methylcyclohexyl-2,2-dicyanoethylene (d) the following compounds are obtained:

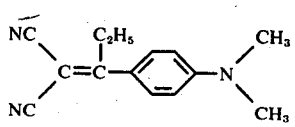
(a)

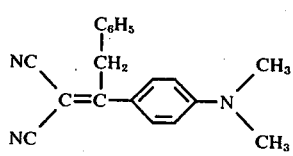
(b)

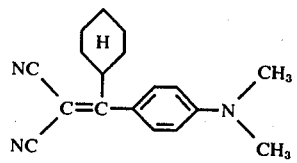
(c)

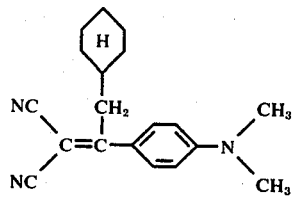
(d)

EXAMPLE 3

24.2 parts of dimethylaniline are dissolved in 50 parts of dry chlorobenzene and the solution is warmed to 40° C. Since the addition of the subsequent reaction components leads to an exothermic reaction, the heating is switched off and the addition is metered in such a way that the temperature of the reaction mixture does not exceed 60° C and the addition of each new component is delayed until the temperature of the reaction has again dropped to 40° C.

The solution of the dimethylaniline is reacted stepwise in the following manner:

1st Step: 22.4 parts of a 50% strength solution of 1-chloro-2,2-dicyanoethylene are added dropwise (reaction component A). 10.0 parts of triethylamine are then added dropwise under the conditions described above (reaction component B).

2nd Step: Under the same conditions as in Step 1, 11.2 parts of the reaction component A are added dropwise, followed by 5.0 parts of the reaction component B.

3rd Step: Under the same conditions and in the same sequence as in Step 1, 5.6 parts of the reaction component A and 2.5 parts of the reaction component B are added dropwise.

4the Step: Analogously to Step 1, 2.8 parts of the reaction component A and 1.25 parts of the reaction component B are added dropwise.

5th Step: Analogously to Step 1, 1.4 parts of the reaction component A and 0.62 part of the reaction component B are added dropwise.

6th Step: Analogously to Step 1, 0.7 part of the reaction component A and 0.3 part of the reaction component B are added dropwise.

At this step, the reaction is dropped since the degree of conversion of the dimethylaniline is 98.4%. The reaction mixture is stirred for a further 2 hours at 50° C and the solvent is then removed under reduced pressure. The residue is washed with water until it is free of the triethylamine hydrochloride produced and is filtered off and dried in vacuo at 90° C to 100° C. In this way, 33.5 parts of the compound of the formula

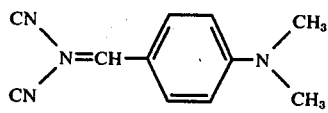

(melting point 177°–179° C) are obtained. If the compound is crystallised from ethanol, glistening red needles (melting point 179°–180° C) are obtained.

EXAMPLE 4

If in Example 3 the 24.2 parts of dimethylaniline are replaced by 59.6 parts of the compound of the formula

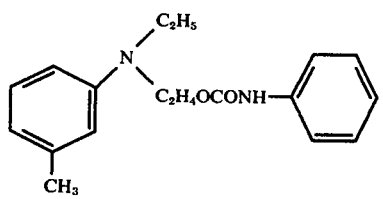

and in other respects the same procedure is followed, 64.5 parts of the compound of the formula

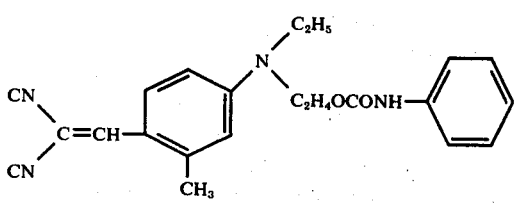

(melting point 128°–134° C) are obtained. If the compound is crystallised from a little ethanol, an analytically pure product (melting point 142° C) is obtained.

EXAMPLE 5

If the 24.2 parts of dimethylaniline in Example 3 are replaced by 46.9 parts of the compound of the formula

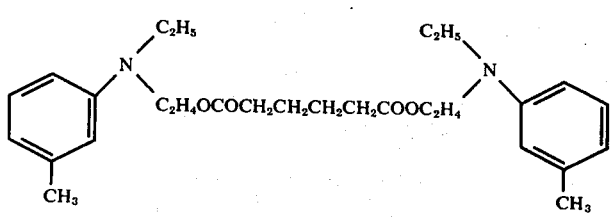

and in other respects the same procedure as in the abovementioned example is followed, 52.5 parts of the compound of the formula

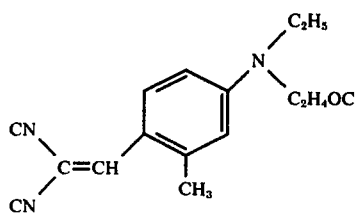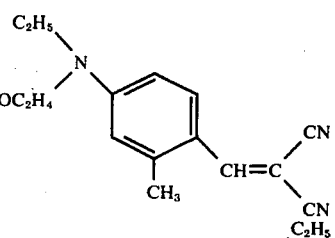

(melting point 97°–100° C) are obtained. If the compound is crystallised from a little ethanol, an analytically pure product (melting point 132° C) is obtained.

EXAMPLE 6

If the 24.2 parts of dimethylaniline in Example 3 are replaced by 74.8 parts of the compound of the formula

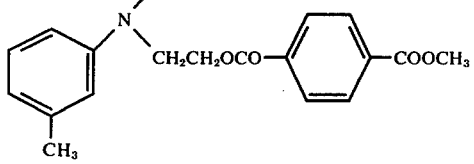

and in other respects the same procedure as in the abovementioned example is followed, 71.0 parts of the compound of the formula

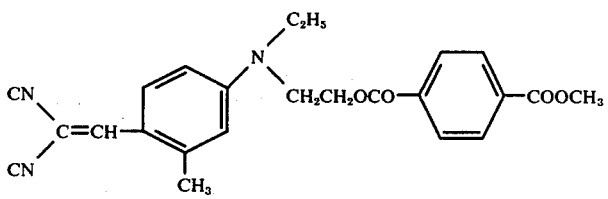

(melting point 142° C) are obtained.

EXAMPLE 8

If the 24.5 parts of dimethylaniline in Example 3 are replaced by 56.6 parts of the compound of the formula

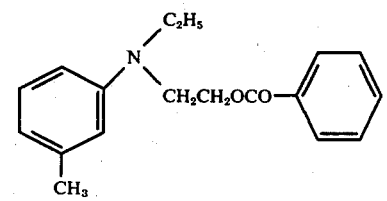

and in other respects the same procedure as in the abovementioned example is followed, 61.2 parts of the compound of the formula

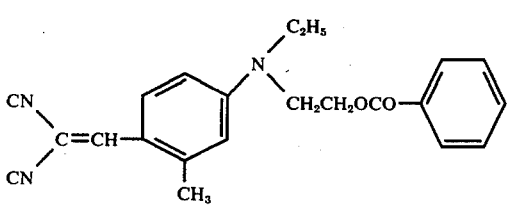

(melting point 112°.C) are obtained.

EXAMPLE 9

If the 24.5 parts of dimethylaniline in Example 3 are replaced by 73.1 parts of the compound of the formula

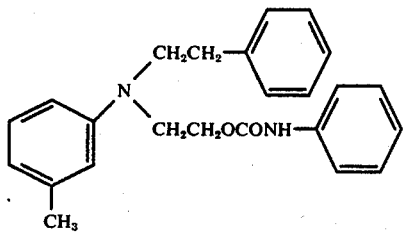

and in other respects the same procedure as in the abovementioned example is followed, 76.5 parts of the compound of the formula

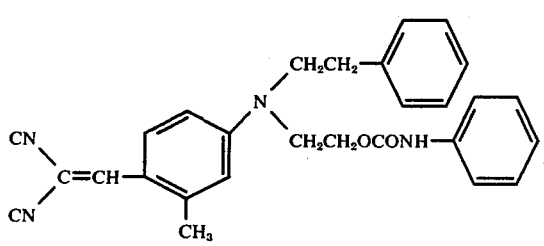

(melting point 147°–149° C) are obtained.

EXAMPLE 7

If the 24.5 parts of dimethylaniline in Example 3 are replaced by 68.2 parts of the compound of the formula

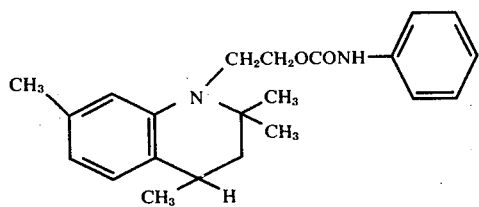

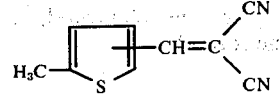

is obtained. If instead of 6.8 parts of furane 17.4 parts of 1-phenyl-3-methyl-5-pyrazolone are employed, the product obtained is a mixture of the compounds

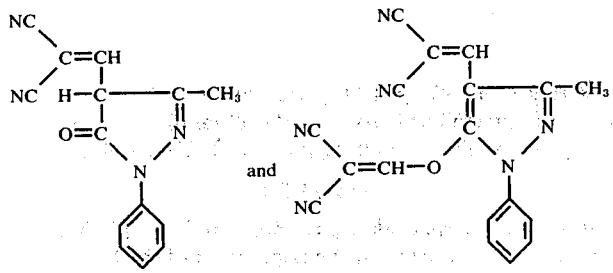

and in other respects the same procedure as in the abovementioned example is followed, 77.5 parts of the compound of the formula

EXAMPLE 11

If the 6.8 parts of furane in Example 10 are replaced by 8.2 parts of 2-methylfurane and otherwise the same procedure as in the abovementioned example is followed, 7.5 parts of a crude compound of the formula

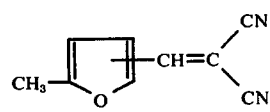

(melting point 75–80° C) are obtained.

If the product is recrystallised from ligroin, yellowish crystals of an analytically pure product (melting point 93° C) are obtained.

The reaction takes place in the same manner if instead of the anhydrous chlorobenzene ethylene chloride, glacial acetic acid or tetrahydrofurane are used.

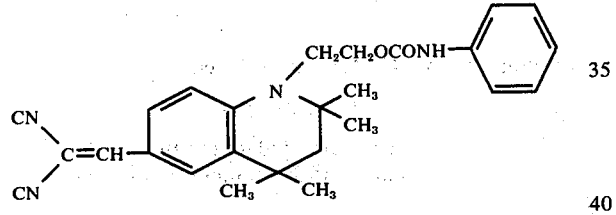

(melting point 181° C) are obtained.

EXAMPLE 10

6.8 parts of furane are dissolved in 50 parts of anhydrous chlorobenzene. The solution is cooled to 0° C and at this temperature 22.4 parts of a 50% strength solution of 1-chloro-2,2-dicyanoethylene in chlorobenzene are added dropwise. The reaction mixture is slowly allowed to warm up to room temperature and is left to react further overnight, whilst stirring. Thereafter the crystal paste is filtered off, and the filter residue is then washed with a little chlorobenzene and is dried in vacuo at 70° C. In this way, 9 parts of a crude compound of the formula Following the procedure of Example 10 and 11, the CH-acid compounds indicated in Column I analogously yield the dicyanovinyl compounds indicated in Column II. Ethylene chloride, glacial acetic acid or tetrahydrofurane are used as solvents.

| I | II |
|---|---|
| $CH_3-\overset{O}{\underset{\|\|}{C}}-CH_2COOC_2H_5$ | 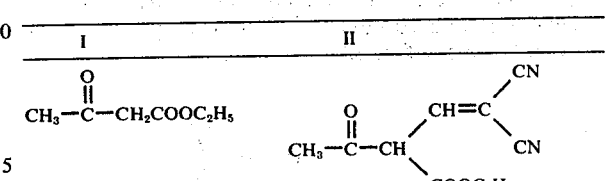 |
| $NC-CH_2-COOC_2H_5$ | 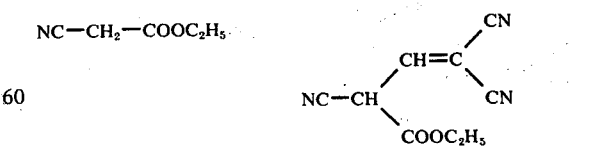 |
| 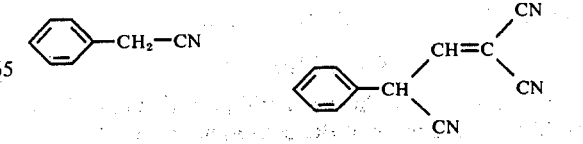 | |

(melting point 160°–170° C) are obtained.

If the product is recrystallised from ethanol, yellowish crystals (melting point 193° C, with decomposition) are obtained. If the 6.8 parts of furane are replaced by 9.5 parts of 2-methylthiophene and otherwise the same procedure is followed, a crude compound of the formula

| I | II |
|---|---|
| 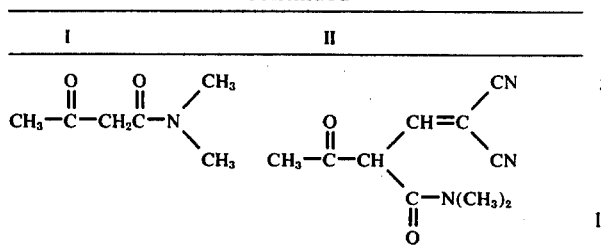 | |

What is claimed is:

1. A process for the manufacture of a compound of the formula

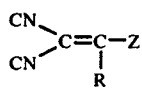

comprising the step of treating a compound, ZH, with a compound of the formula

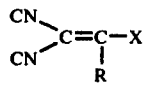

in an anhydrous organic solvent, in the absence of a Lewis acid, wherein

R is hydrogen, $C_1$-$C_4$ alkyl, cyclohexyl or benzyl;
X is chloro or bromo; and
ZH is a compound of the formula

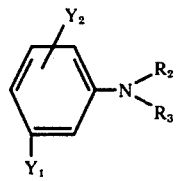

wherein $Y_1$ hydrogen, lower alkyl or lower alkoxy;
$Y_2$ is hydrogen, lower alkyl, lower alkoxy, lower alkanoylamino, lower alkoxycarbonylamino, benzoylamino, chloro or trifluoromethyl; and
$R_3$ and $R_2$ independently represent lower alkyl, cycloalkyl, aryl, or lower alkyl substituted by aryl, cycloalkyl, lower alkoxy, lower alkylcarbonyloxy, lower alkylaminocarbonyloxy, arylcarbonyloxy, arylaminocarbonyloxy, cyano or chloro, and wherein aryl is phenyl or tolyl and cycloalkyl is cyclohexyl, and wherein lower denotes 1 to 4 carbon atoms in the alkyl moiety.

2. The process of claim 1, wherein triethylamine is added to the treatment medium.

3. The process of claim 1, wherein the organic solvent has a dielectric constant which is less than 15.

4. The process of claim 1, wherein the organic solvent is selected from the group consisting of chlorobenzene, ethylenechloride, diethyl ether, and glacial acetic acid.

5. The process of claim 1, wherein the treatment is carried out at a temperature of 0° to 200° C.

6. The process of claim 5, wherein the treatment is carried out at a temperature of the range of 20° to 140° C.

7. The process of claim 1, wherein the compound of formula ZH is used in a stoichiometric amount.

8. The process of claim 1, wherein the compound of formula ZH is used in a 2-fold to 3-fold excess.

* * * * *